US011103192B2

(12) United States Patent
Tsai et al.

(10) Patent No.: US 11,103,192 B2
(45) Date of Patent: Aug. 31, 2021

(54) ECG SIGNAL LOSSLESS COMPRESSION SYSTEM AND METHOD FOR SAME

(71) Applicant: National Central University, Taoyuan (TW)

(72) Inventors: Tsung-Han Tsai, Taoyuan (TW); Wei-Ting Kuo, Yunlin County (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 292 days.

(21) Appl. No.: 16/241,197

(22) Filed: Jan. 7, 2019

(65) Prior Publication Data

US 2020/0046298 A1 Feb. 13, 2020

(30) Foreign Application Priority Data

Aug. 10, 2018 (TW) .................................. 107127934

(51) Int. Cl.
*A61B 5/00* (2006.01)
*A61B 5/318* (2021.01)
*A61B 5/316* (2021.01)

(52) U.S. Cl.
CPC .......... *A61B 5/7232* (2013.01); *A61B 5/0006* (2013.01); *A61B 5/318* (2021.01); *A61B 5/316* (2021.01); *A61B 5/7203* (2013.01)

(58) Field of Classification Search
None
See application file for complete search history.

(56) References Cited

U.S. PATENT DOCUMENTS 6,477,280 B1 * 11/2002 Malvar .................. H03M 7/40
375/E7.047
8,315,709 B2 * 11/2012 Corndorf ............. A61N 1/3702
607/60

* cited by examiner

*Primary Examiner* — Erica S Lee
(74) *Attorney, Agent, or Firm* — Muncy, Geissler, Olds & Lowe, P.C.

(57) ABSTRACT

An ECG signal lossless compression system includes: a signal difference value generating module and a compression module. The signal difference value generating module performs an adaptive linear prediction encoding on an ECG signal, so as to generate a plurality of signal difference values corresponding to each datum of the ECG signal; the compression module divides the signal difference values into a plurality of groups and performs an adaptive linear lossless compression encoding on each group, so as to generate a plurality of window compression streams, wherein each group corresponds to a bit reference index configured to be a compression encoding parameter of the adaptive linear lossless compression encoding.

12 Claims, 9 Drawing Sheets

ECG SIGNAL LOSSLESS COMPRESSION SYSTEM AND METHOD FOR SAME

BACKGROUND OF THE INVENTION

Field of the Invention

The present disclosure relates to a signal compression system and method and, more particularly, to an ECG signal lossless compression system and method.

Description of the Prior Art

As a population ages, incidence of cardiovascular diseases increases, elevating the demand for home care. ECG (electrocardiogram) is an important tool for diagnosing cardiovascular diseases. In case of arrhythmias, which always happen suddenly and unexpectedly, ECG signals are measured with portable, miniaturized and home-friendly ECG signal measuring devices, and then the measured ECG signals are transmitted to a medical apparatus or a cloud database.

Long use of the ECG signal measuring devices leads to generation of abundant datums. The abundant datums take up much storage space. Furthermore, transmission of the ECG signals to a medical apparatus or a cloud database requires heavy network traffic. Last but not least, no medical apparatus is intended to receive datums from just one patient; hence, the entire medical mechanism is overburdened whenever a lot of patients are using home-friendly measuring products.

In view of this, the present disclosure provides an ECG signal lossless compression system and method to overcome aforesaid drawbacks of the prior art, that is, abundant datums generated by the ECG signal measuring devices takes up much storage space, and transmission of the ECG signals requires heavy network traffic.

SUMMARY OF THE INVENTION

It is an objective of the present disclosure to provide an ECG signal lossless compression system which comprises a signal difference value generating module and a compression module. The signal difference value generating module adjusts, according to a plurality of datums preceding one of datums of an ECG signal, an encoding mechanism of an adaptive linear prediction encoding corresponding to the one of datums and encodes the one of datums according to the encoding mechanism, so as to generate a signal difference value corresponding to each subsequent datum of the ECG signal. The compression module divides the signal difference values into a plurality of adaptive linear windows, with each said adaptive linear window comprising a specific number of signal difference values, and performs an adaptive linear lossless compression encoding on the adaptive linear windows to achieve encoding, so as to generate a plurality of window compression streams, wherein each said adaptive linear window corresponds to a bit reference index configured to be a compression encoding parameter of the adaptive linear lossless compression encoding.

Another objective of the present disclosure is to provide an ECG signal lossless compression method, performed with an ECG signal lossless compression system, the method comprising the steps of: adjusting, by a signal difference value generating module, an encoding mechanism of an adaptive linear prediction encoding corresponding to one of datums of an ECG signal according to a plurality of datums preceding the one of datums and encoding, by the signal difference value generating module, the one of datums according to the encoding mechanism, so as to generate a signal difference value corresponding to each datum of the ECG signal; and dividing, by a compression module, the signal difference values into a plurality of adaptive linear windows, with each said adaptive linear window including a specific number of said signal difference values, and performing, by the compression module, an adaptive linear lossless compression encoding on the adaptive linear windows, so as to generate a plurality of window compression streams, wherein each said adaptive linear window corresponds to a bit reference index configured to be a compression encoding parameter of the adaptive linear lossless compression encoding.

DETAILED DESCRIPTION OF THE EMBODIMENTS

The implementation aspects and operation principles of a measuring apparatus of the present disclosure are hereunder described by embodiments. The embodiments enable persons skilled in the art to gain insight into the features and advantages of the present disclosure and thus combine, modify, replace and apply the embodiments according the spirit embodied in the present disclosure.

The verb "connect" used herein includes "connect directly" and "connect indirectly", and is not restrictive of the present disclosure. The expressions "when . . . " and "as soon as . . . " used herein means "at the present moment", "before" or "after", and is not restrictive of the present disclosure. In the situation where the present disclosure discloses advantages (or components), if the word "or" is placed between the words "advantages (or components)," it means that the advantages (or components) are independent of each other, though this does not exclude the possibility of co-existence of the advantages (or components). Furthermore, unless specified otherwise, ordinal numbers, such as "first" and "second", used herein shall not be interpreted in such a manner to mean explicitly or implicitly that the ordinal numbers are descriptive of components or embodiments, nor do the ordinal numbers indicate the sequence of a component or embodiment and another component or embodiment. The ordinal numbers used herein are merely intended to distinguish different components or embodiments. The use of the ordinal numbers herein does not necessarily mean that the present disclosure discloses only the components or embodiments.

Figure 1A:
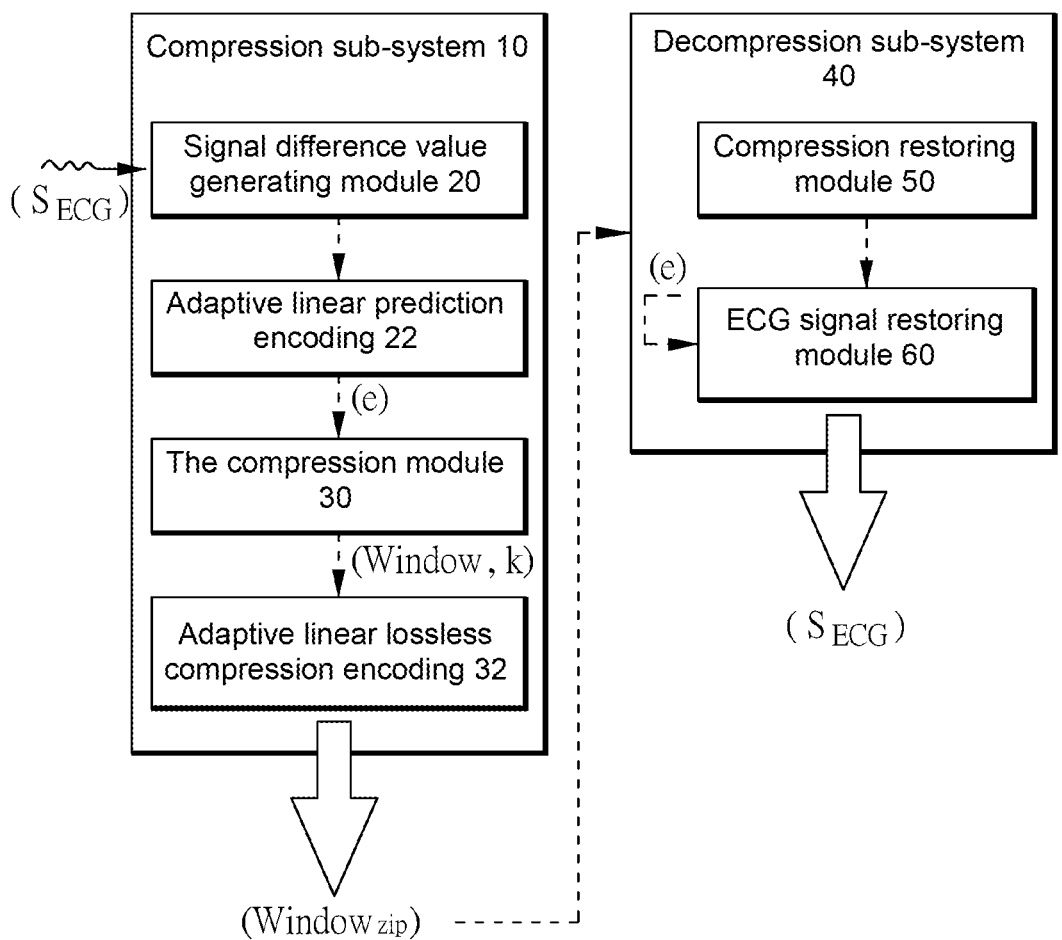
FIG. 1(A) is a block diagram of an ECG signal lossless compression system according to an embodiment of the present disclosure.

FIG. 1(A) is a block diagram of an ECG signal lossless compression system 1 according to an embodiment of the present disclosure. As shown in FIG. 1(A), the ECG signal lossless compression system 1 comprises a signal difference value generating module 20 and a compression module 30. The signal difference value generating module 20 and the compression module 30 are disposed on a compression sub-system 10.

The signal difference value generating module 20 performs a differential encoding or an adaptive linear prediction encoding 22 on an ECG signal $S_{ECG}$. Specifically speaking, the signal difference value generating module 20 performs the differential encoding on a plurality of initial datums (for example, several preceding datums) of the ECG signal $S_{ECG}$, and performs the adaptive linear prediction encoding on datums other than the initial datums. The signal difference value generating module 20 adjusts, according to a plurality of preceding datums of one of datums, an encoding mechanism of the adaptive linear prediction encoding 22 corresponding to the datum, and encodes the datum according to the encoding mechanism. Therefore, the signal difference value generating module 20 generates a signal difference value e corresponding to each datum of the ECG signal $S_{ECG}$. The aforesaid datum is, for example, signal amplitude at an instantaneous point in time, but the present disclosure is not limited thereto.

The compression module 30 divides the signal difference values e into a plurality of adaptive linear windows Window, with each adaptive linear window Window comprising a specific number of the signal difference values e, and performs an adaptive linear lossless compression encoding 32 on the adaptive linear windows Window to achieve compression encoding, so as to generate a plurality of window compression streams $Window_{zip}$. Each adaptive linear window Window has a bit reference index k. The bit reference index k is configured to be a compression encoding parameter of the adaptive linear lossless compression encoding; hence, each window compression stream $Window_{zip}$ corresponds to an adaptive linear window Window and a bit reference index k. The compression module 30 performs compression encoding on a plurality of initial datums of the ECG signal $S_{ECG}$ according to an encoding mechanism of differential encoding, so as to generate the signal difference values e corresponding to the initial datums.

In an embodiment, the ECG signal lossless compression system 1 further comprises a decompression sub-system 40. The decompression sub-system 40 comprises a compression restoring module 50 and an ECG signal restoring module 60. The compression restoring module 50 restores, according to the bit reference index k corresponding to each window compression stream $Window_{zip}$, the signal difference values e compressed and encoded in the window compression stream $Window_{zip}$. The ECG signal restoring module 60 restores the signal difference values e to the ECG signal $S_{ECG}$. The ECG signal restoring module 60 restores the signal difference values e of the initial datums by the decoding technique of differential encoding and restores the signal difference values e of datums other than the initial datums by the decoding technique of the adaptive linear prediction encoding 22.

Figure 1B:
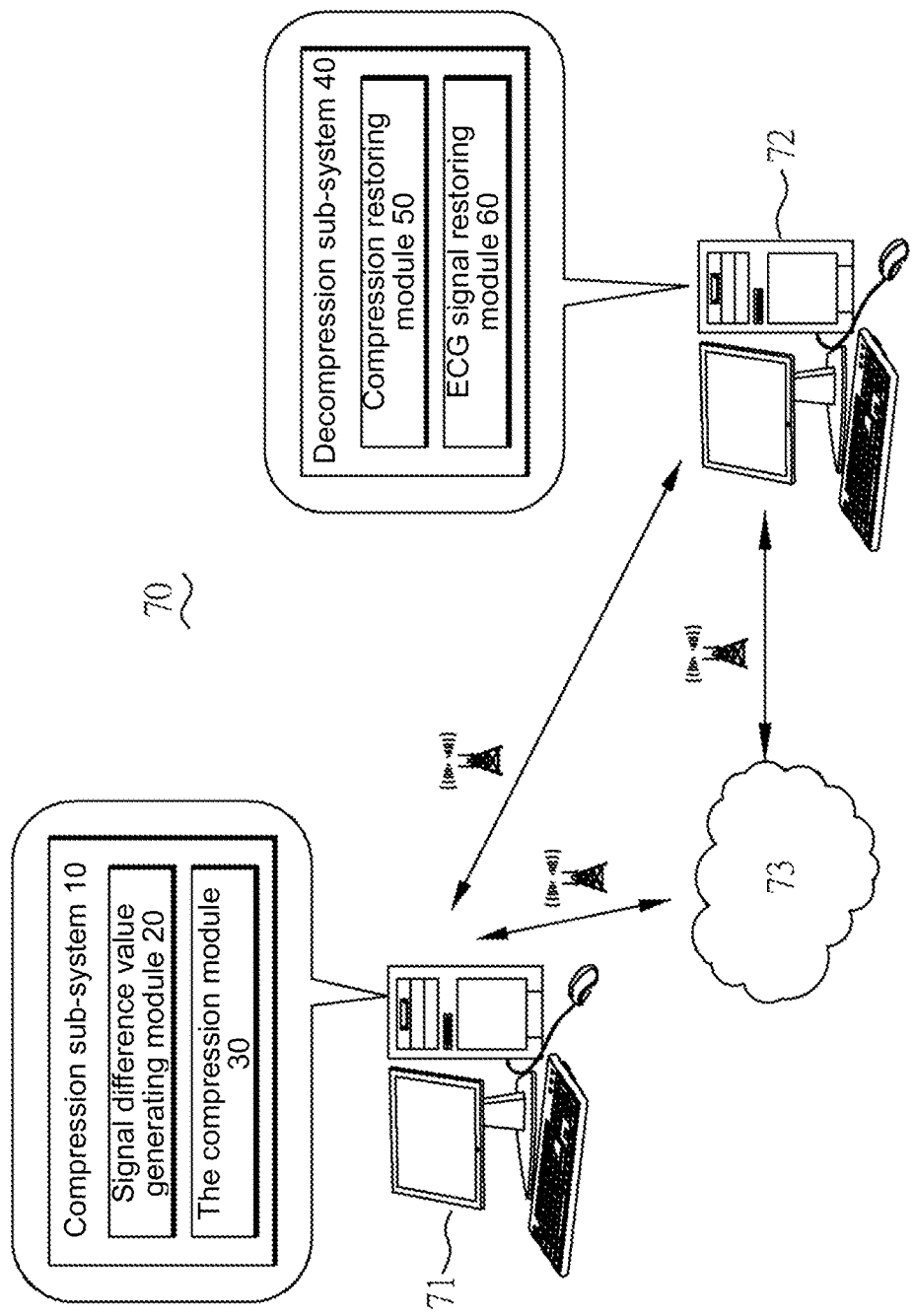
FIG. 1(B) is a schematic view of how the ECG signal lossless compression system of FIG. 1(A) works.

FIG. 1(B) is a schematic view of how the ECG signal lossless compression system 1 of FIG. 1(A) works. As shown in FIG. 1(B), the ECG signal lossless compression system 1 is applied to a remote health management system 70. The remote health management system 70 is divided into a measuring end (such as a patient end) and a management end (such as a physician end). In an embodiment, the compression sub-system 10 is implemented as an electronic apparatus 71 at the measuring end (such as the patient end), for example, a smartphone, a tablet, a desktop, a laptop, a smart bracelet, a smart watch, a signal processor, a motherboard or any apparatus which comes with a microprocessor, to compress the ECG signals measured with a measuring apparatus. Alternatively, the compression sub-system 10 is the measuring apparatus itself, but the present disclosure is not limited thereto. The decompression sub-system 40 is implemented as an electronic apparatus 72 at the management end (such as the physician end), for example, a smartphone, a tablet, a desktop, a laptop, a smart bracelet, a smart watch, a signal processor, a motherboard or any apparatus which comes with a microprocessor, at the physician end, to decompress datums (for example, the window compression streams) from the compression sub-system 10 and thus restore the datums to the ECG signals, but the present disclosure is not limited thereto. In an embodiment, the compression sub-system 10 and the decompression sub-system 40 are capable of networking to therefore transmit datums. In an embodiment, the compression sub-system 10 connects to a cloud server 73 to transmit datums to the cloud server 73, whereas the decompression sub-system 40 downloads datums from the cloud server 73, but the present disclosure is not limited thereto.

The signal difference value generating module 20, compression module 30, compression restoring module 50 and ECG signal restoring module 60 are implemented as hardware or software. When implemented as hardware, the signal difference value generating module 20 and the compression module 30 are electronic circuits with special functions or hardware devices capable of executing special firmware or software (such as a microprocessor of the electronic apparatus 71 at the measuring end). Alternatively, the compression restoring module 50 and the ECG signal restoring module 60 are electronic circuits with special functions or hardware devices capable of executing special firmware or software (such as a microprocessor of the electronic apparatus 72 at the management end), but the present disclosure is not limited thereto. When implemented as software, the signal difference value generating module 20, compression module 30, compression restoring module 50 and ECG signal restoring module 60 are implemented as computer program products composed of program code. When the computer program products are loaded into a microcontroller or a microprocessor of the electronic devices (such as the electronic apparatus 71 at the measuring end or the electronic apparatus 72 at the management end), the microcontroller or the microprocessor performs special operations; hence, the modules are also regarded as special-function modules in the microcontroller or the microprocessor. In an embodiment, the signal difference value generating module 20, compression module 30, compression restoring module 50 and ECG signal restoring module 60 are either implemented as programs independent of each other or integrated into the same program. The program codes of the signal difference value generating module 20, compression module 30, compression restoring module 50 and ECG signal restoring module 60 are compiled in any type of programming language, but the present disclosure is not limited thereto. In an embodiment, the signal difference value generating module 20, compression module 30, compression restoring module 50 and ECG signal restoring module 60 are pre-stored outside electronic devices (such as the electronic apparatus 71 at the measuring end or the electronic apparatus 72 at the management end), for example, pre-stored in a cloud server or a non-transient computer-readable medium, such as a compact disk, a hard disk drive, or a USB flash drive, and then installed on the electronic devices later.

Figure 2A:
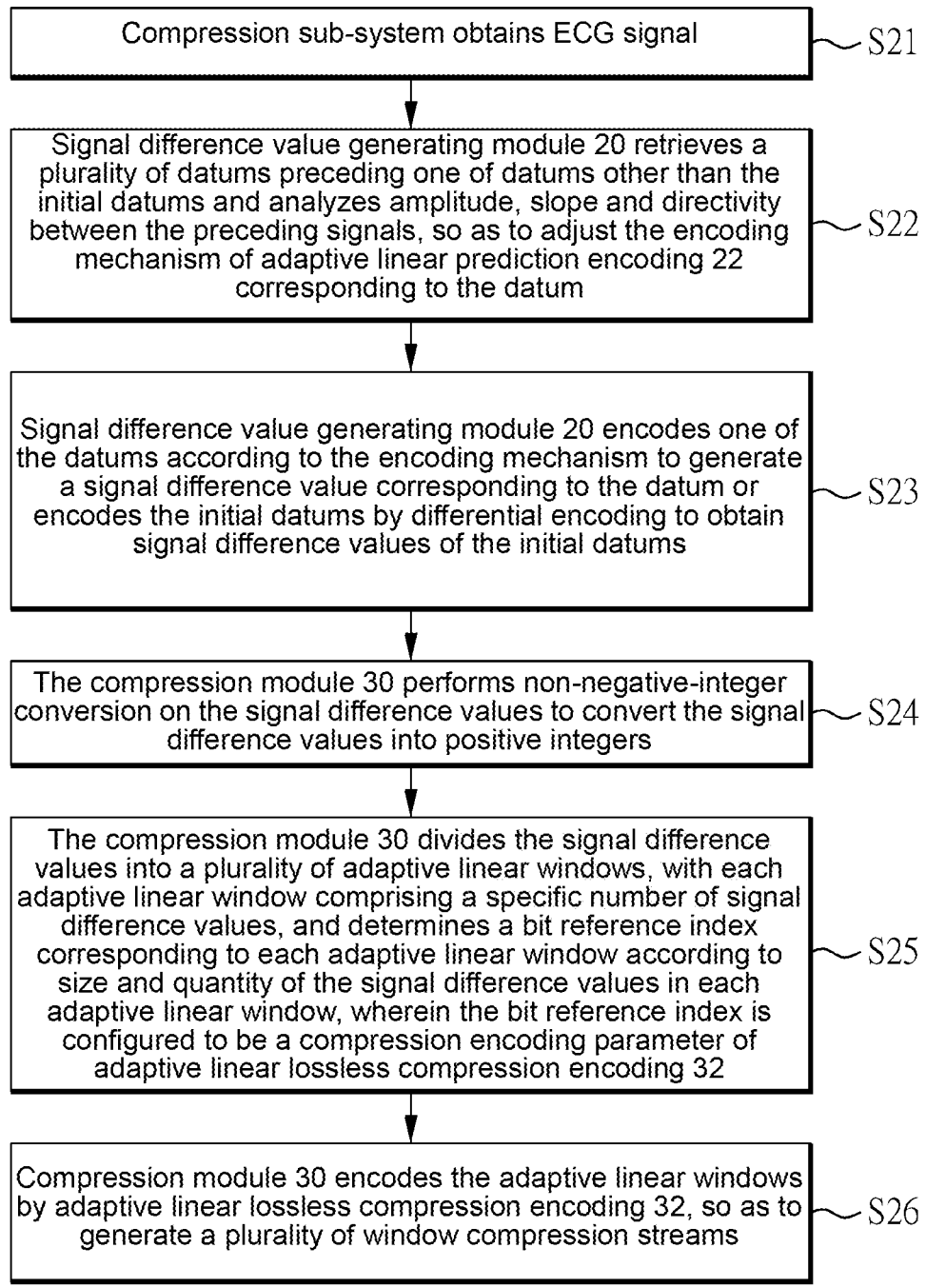
FIG. 2(A) is a flowchart of an ECG signal lossless compression method according to the first embodiment of the present disclosure.

Operations performed with the signal difference value generating module 20 and the compression module 30 of the compression sub-system 10 are explained below. Referring to FIGS. 1(A) to 2(A), wherein FIG. 2(A) is a flowchart of an ECG signal lossless compression method according to the first embodiment of the present disclosure to depict the process flow of operation of the compression sub-system 10.

First, step S21 is carried out, wherein the compression sub-system 10 obtains an ECG signal $S_{ECG}$. The ECG signal $S_{ECG}$ comprises a plurality of datums (for example, instantaneous amplitudes), and the datums include a plurality of initial datums. Afterward, step S22 is carried out, wherein the signal difference value generating module 20 retrieves a plurality of datums preceding one of datums other than the initial datums and analyzes amplitude, slope and directivity between the preceding signals, so as to adjust an encoding mechanism of the adaptive linear prediction encoding 22 corresponding to the one of datums. Afterward, step S23 is carried out, wherein the signal difference value generating module 20 encodes the one of datums according to the encoding mechanism, so as to generate the signal difference value e corresponding to the one of datums. Alternatively, the signal difference value generating module 20 encodes the initial datums by differential encoding, so as to obtain the signal difference values e of the initial datums. Afterward, steps S22 to S23 are performed again until the signal difference values e corresponding to all of datums of the ECG signal $S_{ECG}$ are generated. Afterward, step S24 is carried out, wherein the compression module 30 performs a non-negative-integer conversion on the signal difference values e, so as to convert the signal difference values e into positive integers. Afterward, step S25 is carried out, wherein the compression module 30 divides the signal difference values e into a plurality of adaptive linear windows Window, with each adaptive linear window Window comprising a specific number of the signal difference values e, and determines the bit reference index k of each adaptive linear window Window according to the size and quantity of the signal difference values e in each adaptive linear window Window. The bit reference index k is configured to be a compression encoding parameter of the adaptive linear lossless compression encoding 32. Afterward, step S26 is carried out, wherein the compression module 30 encodes the adaptive linear window Window by the adaptive linear lossless compression encoding 32, so as to generate a plurality of window compression streams $Window_{zip}$. Therefore, the ECG signal $S_{ECG}$ is compressed efficiently and losslessly, thereby taking up little storage space and taking up little network bandwidth.

In an embodiment that illustrates step S21, the compression sub-system 10 is connected to a measuring device; hence, as soon as the measuring device finishes measuring the ECG signal $S_{ECG}$ of a subject, such as a patient, the ECG signal $S_{ECG}$ is transmitted to the compression sub-system 10 or a cloud server 70 such that the compression sub-system 10 can obtain the ECG signal $S_{ECG}$. In another embodiment, the compression sub-system 10 integrates with the measuring device and thus directly obtains the ECG signal $S_{ECG}$.

In steps S22 to S23, after the compression sub-system 10 has obtained the ECG signal $S_{ECG}$, the signal difference value generating module 20 performs first-instance encoding on each datum (for example, instantaneous amplitude) of the ECG signal $S_{ECG}$ to generate the corresponding signal difference value (which occupies a small byte) from the original value (which occupies a large byte) of each datum and thus reduce the datums of the ECG signal $S_{ECG}$ beforehand, thereby enhancing the efficiency of subsequent compression (steps S24 to S26).

The ECG signal $S_{ECG}$ consists of a P wave, a QRS complex, a T wave and a U wave, which vary in slope and amplitude. If all the datums of the ECG signal $S_{ECG}$ undergoes first-instance encoding by the conventional differential encoding, erroneous difference values will be generated. To overcome this drawback, the present disclosure is advantageous in that the encoding rules of the adaptive linear prediction encoding 22 vary from datum to datum to therefore greatly reduce erroneous difference values. Furthermore, the initial datums lack sufficient preceding datums, and thus the signal difference value generating module 20 still performs conventional differential encoding (the conventional differential encoding not only allows the first initial datum to keep its original datum, but also involves encoding every other initial datum according to the difference value between the initial datum and the preceding initial datum, but the present disclosure is not limited thereto) on the initial datums. By contrast, datums other than the initial datums have sufficient preceding datums and thus undergo the adaptive linear prediction encoding.

In order to achieve the above and other objectives, in an embodiment of step S22, to perform the adaptive linear prediction encoding on a datum other than the initial datums, the signal difference value generating module 20 retrieves datums which precede the datum, determines waveform characteristics, such as crests, troughs, steep slopes and gentle slopes, of the preceding datums according to amplitude, slope and directivity between the preceding datums, and thus selects an encoding mechanism of the adaptive linear prediction encoding suitable for the datum, so as to reduce wrong difference values which might otherwise be generated in the subsequent encoding process. The position of the datum in a waveform can be accurately determined only when sufficient preceding datums are available; hence, in an embodiment, at least four preceding datums are required. Therefore, the fifth datum of the ECG signal $S_{ECG}$ and subsequent datums thereof undergo the adaptive linear prediction encoding, whereas the first four datums of the ECG signal $S_{ECG}$ are configured to be initial datums and undergo differential encoding.

Figure 2B:
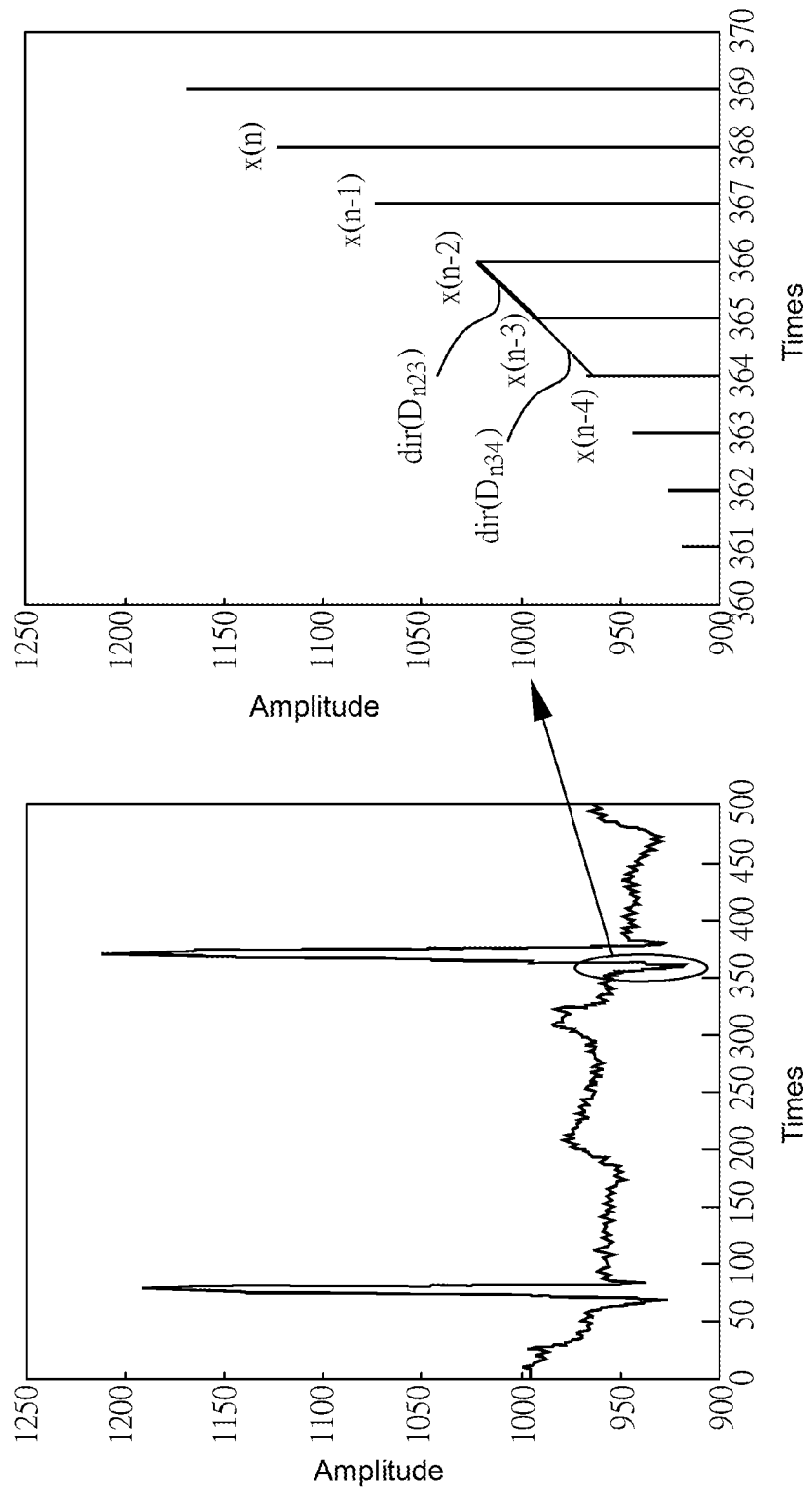
FIG. 2(B) is a schematic view of ECG signals according to an embodiment of the present disclosure.

The way the signal difference value generating module 20 determines the characteristics of the preceding datums in a waveform is hereunder illustrated by an embodiment. FIG. 2(B) is a schematic view of the ECG signal $S_{ECG}$ according to an embodiment of the present disclosure. Referring to FIG. 2(A) and FIG. 2(B), as shown in FIG. 2(B), the datum to undergo the adaptive linear prediction encoding is defined as x (n), defining the preceding fourth datum as x (n−4), the preceding third datum as x (n−3), the preceding second datum as x (n−2), and the preceding first datum as x (n−1), wherein the preceding datums indicate amplitudes at different instantaneous points in time, respectively.

In an embodiment, the signal difference value generating module 20 calculates difference values between the preceding datums in order to obtain amplitude, slope and directivity between the preceding datums. In a preferred embodiment, the signal difference value generating module 20 obtains at least four preceding datum difference values $D_{n12}$, $D_{n13}$, $D_{n23}$, $D_{n34}$ and at least two preceding datum slope informations dir ($D_{n34}$), dir ($D_{n23}$), wherein the preceding datum difference values $D_{n12}$, $D_{n13}$, $D_{n23}$, $D_{n34}$ are expressed by equations below, $$D_{n12}=x(n-1)-x(n-2);$$

$$D_{n13}=x(n-1)-x(n-3);$$

$$D_{n23}=x(n-2)-x(n-3); \text{ and}$$

$$D_{n34}=x(n-3)-x(n-4);$$

wherein the preceding datum difference value $D_{n12}$ is the difference value between the preceding first datum x (n−1) and the preceding second datum x (n−2), the preceding datum difference value $D_{n13}$ is the difference value between the preceding first datum x (n−1) and the preceding third datum x (n−3), the preceding datum difference value $D_{n23}$ is the difference value between the preceding second datum x (n−2) and the preceding third datum x (n−3), and the preceding datum difference value $D_{n34}$ is the difference value between the preceding third datum x (n−3) and the preceding fourth datum x (n−4). Furthermore, the preceding datum slope information dir (is the slope between the preceding third datum x (n−3) and the preceding fourth datum x (n−4), whereas the preceding datum slope information dir ($D_{n23}$) is the slope between the preceding second datum x (n−2) and the preceding third datum x (n−3).

After the signal difference value generating module 20 has obtained the preceding datum difference values $D_{n12}$, $D_{n13}$, $D_{n23}$, $D_{n34}$ and the preceding datum slope informations dir ($D_{n23}$), dir ($D_{n34}$), the signal difference value generating module 20 performs an encoding mechanism adjustment method based on Fuzzy decision to adjust an encoding mechanism of the adaptive linear prediction encoding 22 according to the amplitude, slope and directivity between the initial datums.

Figure 2C:
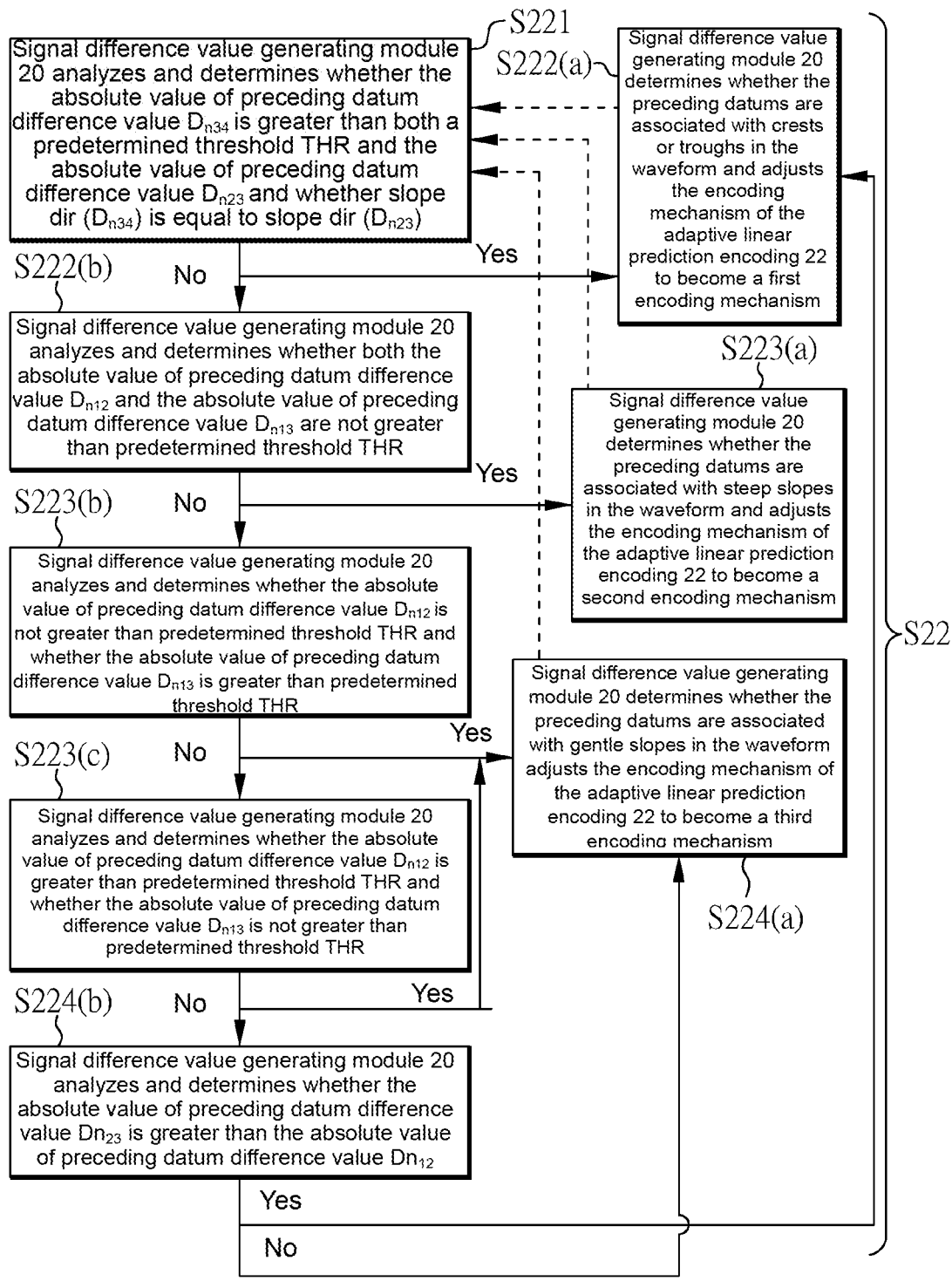
FIG. 2(C) is a flowchart of an encoding mechanism selection method according to an embodiment of the present disclosure.

FIG. 2(C) is a flowchart of an encoding mechanism selection method according to an embodiment of the present disclosure. First, step S221 is carried out, wherein, after the signal difference value generating module 20 has obtained the preceding datum difference values $D_{n12}$, $D_{n13}$, $D_{n23}$, $D_{n34}$ and the preceding slope information dir, the signal difference value generating module 20 analyzes and determines whether the absolute value of preceding datum difference value $D_{n34}$ is greater than both a predetermined threshold THR and the absolute value of preceding datum difference value $D_{n23}$ and whether slope dir ($D_{n34}$) is equal to slope dir ($D_{n23}$) (i.e., whether criteria $|D_{n34}|$>THR, $|D_{n34}|$>$|D_{n23}|$, and dir ($D_{n34}$)=dir ($D_{n23}$ are met.)

Assuming all the criteria in step S221 are met, then step S222(a) is carried out, wherein the signal difference value generating module 20 determines whether the preceding datums are associated with crests or troughs in the waveform and adjusts an encoding mechanism of the adaptive linear prediction encoding 22 corresponding to the datum x (n) to become a first encoding mechanism. In an embodiment, the first encoding mechanism is expressed by the equation below, $$e=x(n)-\{3*x(n-1)-3*x(n-2)+x(n-3)\};$$

wherein e denotes the signal difference value corresponding to the datum x (n).

If one of the criteria in step S221 is not met, step S222(b) will be carried out, wherein the signal difference value generating module 20 analyzes and determines whether both the absolute value of preceding datum difference value $D_{n12}$ and the absolute value of preceding datum difference value $D_{n13}$ are not greater than predetermined threshold THR (i.e., whether criteria $|D_{n12}|$≤THR, and $|D_{n13}|$≤THR are met.)

Assuming all the criteria in step S222(b) are met, then step S223(a) is carried out, wherein the signal difference value generating module 20 determines whether the preceding datums are associated with steep slopes in the waveform and adjusts an encoding mechanism of the adaptive linear prediction encoding 22 corresponding to the datum x (n) to become a second encoding mechanism. In an embodiment, the second encoding mechanism is expressed by the equation below, $$e=x(n)-x(n-1);$$

wherein e denotes the signal difference value corresponding to the datum x (n).

If one of the criteria in step S222(b) is not met, step S223(B) will be carried out, wherein the signal difference value generating module 20 analyzes and determines whether the absolute value of preceding datum difference value $D_{n12}$ is not greater than predetermined threshold THR, and whether the absolute value of preceding datum difference value $D_{n13}$ is greater than predetermined threshold THR (i.e., whether the criteria $|D_{n12}|$≤THR, and $|D_{n13}|$>THR are met.)

Assuming all the criteria in step S223(b) are met, then step S224(a) is carried out, wherein the signal difference value generating module 20 determines whether the preceding datums are associated with gentle slopes in the waveform and adjusts an encoding mechanism of the adaptive linear prediction encoding 22 corresponding to the datum x (n) to become a third encoding mechanism. In an embodiment, the third encoding mechanism is expressed by the equation below, $$e=x(n)-\{2*x(n-1)-x(n-2)\};$$

wherein e denotes the signal difference value corresponding to the datum x (n).

If one of the criteria in step S222(b) is not met, step S223(c) will be carried out, wherein the signal difference value generating module 20 analyzes and determines whether the absolute value of preceding datum difference value $D_{n12}$ is greater than predetermined threshold THR, and whether the absolute value of preceding datum difference value $D_{n13}$ is not greater than predetermined threshold THR (i.e., whether criteria $|D_{n12}|$>THR and $|D_{n13}|$≤THR are met.)

Assuming all the criteria in step S223(b) are met, then step S224(a) is carried out again, wherein the signal difference value generating module 20 determines whether the preceding datums are associated with gentle slopes in the waveform and adjusts an encoding mechanism of the adaptive linear prediction encoding 22 corresponding to the datum x (n) to become a third encoding mechanism.

If one of the criteria in step S222(c) is not met, step S224(b) will be carried out, wherein the signal difference value generating module 20 analyzes and determines whether the absolute value of preceding datum difference value is greater than the absolute value of preceding datum difference value $D_{n12}$ (i.e., whether the criterion $|D_{n23}|$>$|D_{n12}|$ is met.)

Assuming all the criteria in step S224(b) are met, then step S222(a) is carried out again, wherein the signal difference value generating module 20 determines whether the preceding datums are associated with crests or troughs in the waveform and adjusts an encoding mechanism of the adaptive linear prediction encoding 22 corresponding to the datum x (n) to become a first encoding mechanism.

If none of the criteria in step S224(b) is met, step S224(a) will be carried out again, wherein the signal difference value generating module 20 determines whether the preceding datums are associated with gentle slopes in the waveform and adjusts an encoding mechanism of the adaptive linear prediction encoding 22 corresponding to the datum x (n) to become a third encoding mechanism.

Whenever an encoding mechanism is adjusted, step S221 will be carried out again such that the signal difference value generating module 20 begins performing the encoding mechanism adjustment method on the next datum x (n+1).

Therefore, the signal difference value generating module 20 adjusts an encoding mechanism corresponding to datums other than the initial datums. Furthermore, encoding errors are greatly reduced, because the encoding mechanism is adjusted according to waveform characteristics of preceding datums.

In step S23, the signal difference value generating module 20 performs differential encoding on the initial datums to obtain the signal difference values e corresponding to the initial datums and performs the adaptive linear prediction encoding 22 on the other datums according to a corresponding encoding mechanism so as to obtain the signal difference values e corresponding to datums other than the initial datums. Afterward, the signal difference values e are transmitted to the compression module 30 for undergoing compression encoding.

In a preferred embodiment, the adaptive linear lossless compression encoding 32 performed by the compression module 30 on the signal difference values e is a content-adaptive Golomb-Rice coding, such as Golomb Rice coding. The conventional Golomb coding is a lossless datum compression method which is simple and thus more applicable to a microprocessor-equipped embedded system than any other algorithm. However, to allow the microprocessor to perform computation more smoothly, the present disclosure requires Golomb-Rice coding which improves on the conventional Golomb coding and is suitable for use in exponential attenuation probability distribution.

Owing to the characteristics of Golomb-Rice coding, the signal difference values e undergoing compression encoding must be computed in the form of positive integers. Hence, in step S24, the compression module 30 performs a non-negative-integer conversion on the signal difference values e. The non-negative-integer conversion entails, for example, taking the absolute value of the signal difference value e, though performing the other type of computation is also feasible. In a preferred embodiment, the non-negative-integer conversion performed on each signal difference value is expressed by the equation below, $$M = \begin{cases} 2*|e|-1, & e < 0 \\ 2*e, & e \geq 0 \end{cases}$$

wherein M denotes one of the signal difference values resulting from the non-negative-integer conversion (hereinafter referred to as "signal difference value M resulting from conversion").

To render the compression process efficient, step S25 is carried out. The compression module 30 divides the signal difference values e into a plurality of groups, with each group including a specific number of the signal difference values e. Each group is defined as an adaptive linear window Window. Afterward, compression encoding is performed on each adaptive linear window. Furthermore, the compression module 30 determines the bit reference index k of the adaptive linear window Window according to the size and quantity of the signal difference values e in each adaptive linear window Window and configures the bit reference index k to be a compression encoding parameter of the adaptive linear lossless compression encoding 32 (content-adaptive Golomb rice coding), thereby enhancing efficiency of compression.

In an embodiment, quantity of the signal difference values e of each adaptive linear window Window depends on the duration of the QRS complex. For instance, assuming that the QRS complex of an ECG signal $S_{ECG}$ lasts 0.1 second approximately, the magnitude (quantity of the signal difference values e) of each adaptive linear window Window is configured to be 0.1* sampling frequency; meanwhile, assuming that the ECG signal $S_{ECG}$ has a signal frequency of 360 Hz, the magnitude (quantity of the signal difference values e) of each adaptive linear window Window is equivalent to 40 samples (i.e., 40 signal difference values e), but the present disclosure is not limited thereto.

In an embodiment, the bit reference index k of an adaptive linear window Window is expressed by the equation below, $$k = \log 2\left(\frac{\sum_{m=0}^{m=W}|M_m|}{W}\right);$$

wherein k denotes the bit reference index of the adaptive linear window Window, W denotes quantity of the signal difference values e of the adaptive linear window Window, M denotes the signal difference values resulting from conversion, and m denotes sequence of the signal difference values in the adaptive linear window Window, where m is a positive integer.

Afterward, step S26 is carried out, and then step S26 is carried out, wherein the compression module 30 performs the adaptive linear lossless compression encoding 32 on each adaptive linear window Window to achieve compression encoding, so as to generate a plurality of window compression streams $Window_{zip}$. In an embodiment, the encoding result of the adaptive linear lossless compression encoding 32 is divided into a quotient coding portion and a remainder coding portion. The quotient coding portion is encoded by unary code. The remainder coding portion is encoded by binary code. An independent bit (isolated bit) "0" is placed between the quotient coding portion and the remainder coding portion to serve as a reference for judgment made at the decoding end. In an embodiment, the adaptive linear lossless compression encoding 32 is expressed by the equation below, $$\begin{cases} \text{quotient} = \left[\frac{M}{2^k}\right] \\ \text{remainder} = M \mod 2^k \\ \text{isolated bit} = 0 \end{cases}$$

where quotient denotes the quotient coding portion, remainder denotes the remainder coding portion, and isolated bit is an independent bit. The above equation is illustrated with an example below. Assuming if, after conversion, signal difference values M=10, bit reference index k=2, then the quotient portion of the signal difference value is 2 (11 after undergoing unary encoding), and the remainder portion of the signal difference value is 2 ($01_2$ after undergoing binary encoding), and in consequence the result of the compression encoding is "11 0 $01_2$".

Figure 2D:
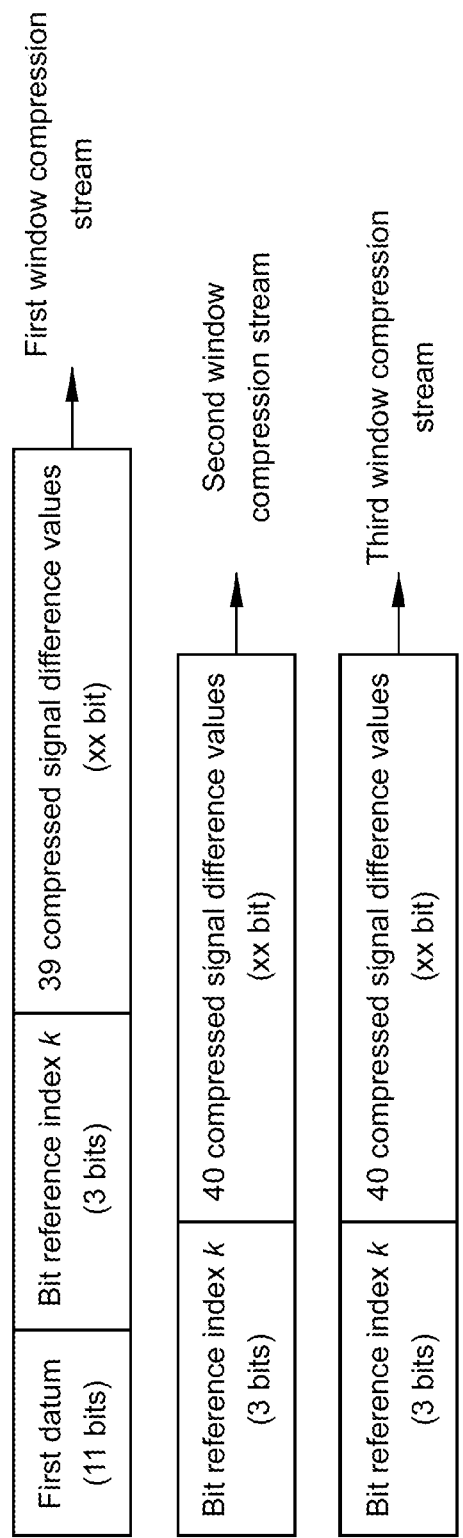
FIG. 2(D) is a schematic view of window compression streams according to an embodiment of the present disclosure.

Therefore, the compression module 30 performs the adaptive linear lossless compression encoding 32 on each adaptive linear window Window, so as to generate each window compression stream $Window_{zip}$, and each window compression stream comprises a plurality of signal difference values M resulting from compression encoding and conversion. FIG. 2(D) is a schematic view of the window compression streams $Window_{zip}$ according to an embodiment of the present disclosure. As shown in FIG. 2(D), ECG signal $S_{ECG}$ undergoes compression encoding to generate a plurality of window compression streams $Window_{zip}$. The first window compression stream comprises an original initial datum not compressed, the bit reference index k corresponding to the window and (W−1) signal difference values M resulting from compression encoding and conversion. The other window compression streams each comprise W signal difference values M resulting from compression encoding and conversion and the bit reference index k corresponding to the window. In an embodiment, the original initial datum is an original datum of the first initial datum of the ECG signal $S_{ECG}$ (that is, an datum not resulting from compression encoding) to serve as reference for use by the decompression sub-system 40 during the signal restoring process. In a preferred embodiment, an original initial datum in the first window compression stream $Window_{zip}$ is stored in the form of 11 bits, and its bit reference index k is stored in the form of three bits, whereas the other datums are stored in the form of a plurality of bits. The bit reference index k in the other window compression streams $Window_{zip}$ is also stored in the form of three bits, whereas the other datums are stored in the form of a plurality of bits, but the present disclosure is not limited thereto.

The signal difference values M resulting from compression and conversion have "datum lossless" characteristics and occupy much less bytes than the original datum, thereby enhancing the ease of storing datums and transmitting datums.

Figure 3A:
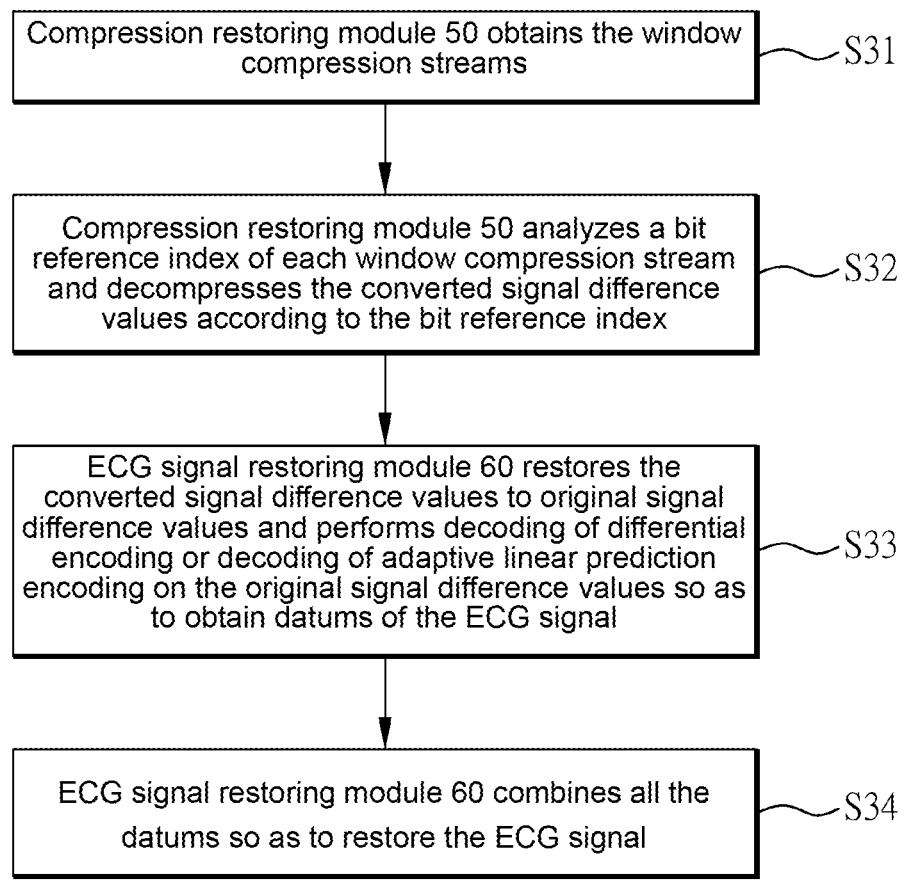
FIG. 3(A) is a flowchart of an ECG signal lossless compression method (decompression) according to the second embodiment of the present disclosure.

Operations performed by the compression restoring module 50 and the ECG signal restoring module 60 of the decompression sub-system 40 are described below. Referring to FIG. 1(A), FIG. 1(B) and FIG. 3(A), wherein FIG. 3(A) is a flowchart of an ECG signal lossless compression method according to the second embodiment of the present disclosure to depict the process flow of the operation of the decompression sub-system 40.

First, step S31 is carried out, wherein the compression restoring module 50 obtains the window compression streams $Window_{zip}$. Afterward, step S32 is carried out, wherein the compression restoring module 50 analyzes the bit reference index k of each window compression stream and obtains the quotient coding portion and the remainder coding portion of each signal difference value M resulting from compression encoding and conversion according to the bit reference index k, so as to obtain each signal difference value M resulting from the non-negative-integer conversion. Afterward, step S33 is carried out, wherein the ECG signal restoring module 60 restores the signal difference values M resulting from conversion to original signal difference values e and performs decoding of differential encoding or decoding of the adaptive linear prediction encoding on the signal difference values e, so as to obtain initial datums of the ECG signal $S_{ECG}$ and datums other than the initial datums. Then, step S34 is carried out, wherein the ECG signal restoring module 60 combines all the datums obtained in step S33, so as to restore the ECG signal $S_{ECG}$.

In an embodiment of step S31, the decompression sub-system 40 communicates with the compression sub-system 10, so as to obtain the window compression streams $Window_{zip}$ of the ECG signal $S_{ECG}$. In another embodiment, the decompression sub-system 40 obtains the window compression streams $Window_{zip}$ from the cloud server 70.

Figure 3B:
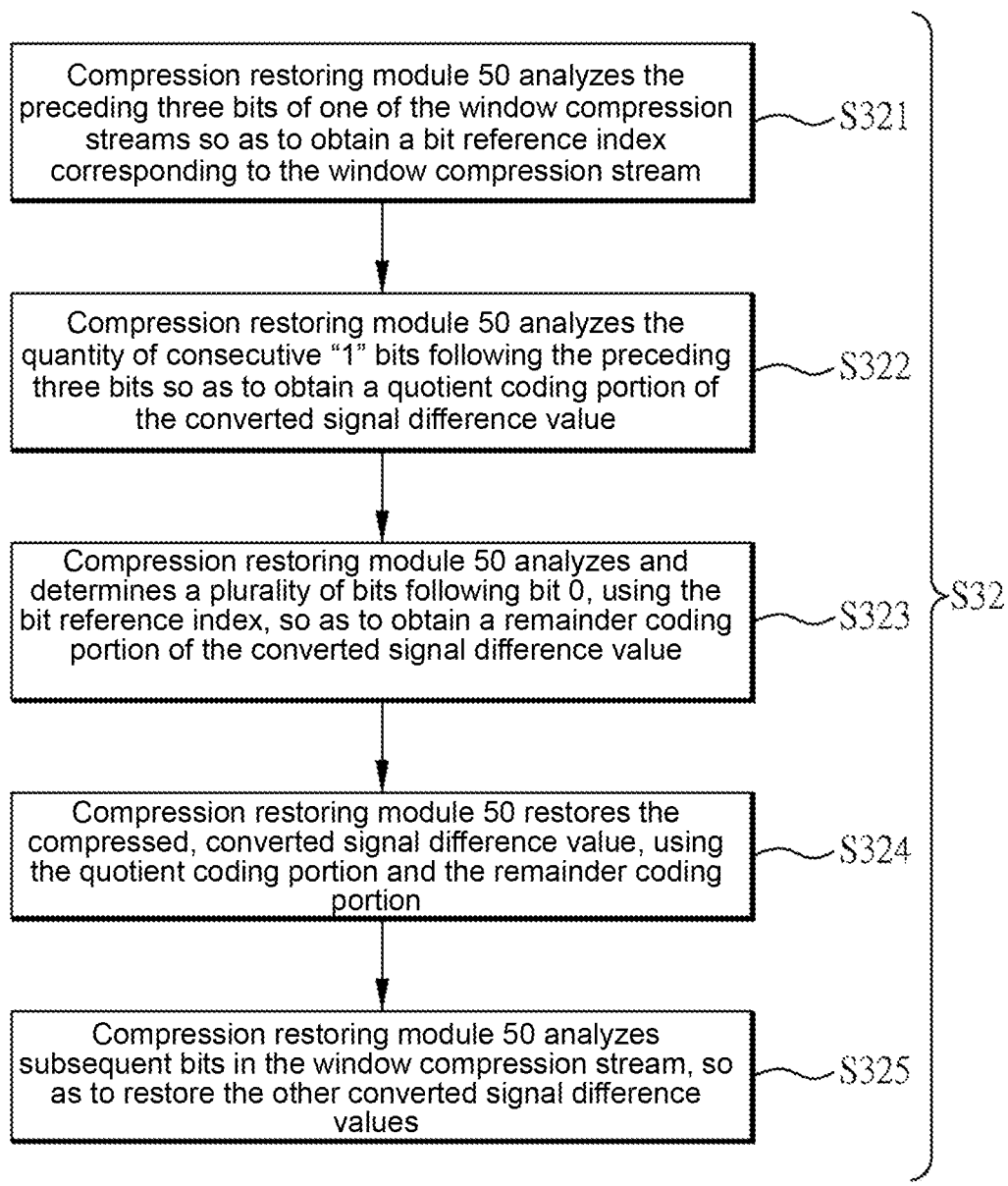
FIG. 3(B) is a flowchart of step S32 according to an embodiment of the present disclosure.

Step S32 is illustrated by an embodiment below. FIG. 3(B) is a flowchart of step S32 according to an embodiment of the present disclosure.

Referring to FIGS. 3(A) and 3(B), step S321 is carried out, wherein the compression restoring module 50 analyzes the first three bits of one of the window compression streams $Window_{zip}$, so as to obtain the bit reference index k corresponding to the window compression stream $Window_{zip}$. For instance, when the compression restoring module 50 receives the window compression stream $Window_{zip}$ "011 1111111 0 010 1111 0 011 . . . ", the compression restoring module 50 converts the first three bits "011" from binary to decimal, and thus the compression restoring module 50 determines that the bit reference index k is 3.

Afterward, step S322 is carried out, wherein the compression restoring module 50 analyzes the number of consecutive "1" bits following the first three bits, so as to obtain the quotient coding portion of the signal difference values M converted. Since the quotient coding portion consists of unary code, it is feasible to obtain information about the quotient coding portion by calculating the number of consecutive "1" bits. For instance, after the compression restoring module 50 has received the window compression stream $Window_{zip}$ "011 1111111 0 010 1111 0 011 . . . ", and after the compression restoring module 50 has determined that the bit reference index k is 3, the compression restoring module 50 counts the number of consecutive "1" bits (i.e., "1111111") following "011", using a loop counting technique. Since the number of consecutive "1" bits is 7, the compression restoring module 50 obtains information about the quotient coding portion of the signal difference values M converted, because "7 times $2^3$ equals 56".

Afterward, step S323 is carried out, wherein the compression restoring module 50 analyzes and determines a plurality of bits following bit "0" according to the bit reference index k, so as to obtain the remainder coding portion of the signal difference values M converted. Owing to an independent bit "0" between the quotient coding portion and the remainder coding portion, the compression restoring module 50 can easily identify the initial points of the bits of the remainder coding portion. Furthermore, since the remainder coding portion depends on the magnitude of the bit reference index k (see step S26), the number of the bits of the remainder coding portion can be determined according to the bit reference index k. For instance, after the compression restoring module 50 has received the window compression stream $Window_{zip}$ "011 1111111 0 010 1111 0 011 . . . ", and the compression restoring module 50 has determined that the bit reference index k is 3 and the quotient coding portion is 56, the bit reference index k (=3) enables the compression restoring module 50 to identify the three bits "010" following the independent bit "0" as the remainder coding portion and thus convert "010" from binary to decimal, so as to determine that the information about the remainder coding portion is 2.

Afterward, step S324 is carried out, wherein the compression restoring module 50 combines the quotient coding portion (i.e., "56") and the remainder coding portion (i.e., "2") to obtain the signal difference values M (i.e., "58") which results from decompression and conversion.

Afterward, step S325 is carried out, wherein the compression restoring module 50 analyzes subsequent bits of the window compression stream Window$_{zip}$ to decompress (restore) the other signal difference values M converted. For instance, after the compression restoring module 50 has received the window compression stream Window$_{zip}$ "011 1111111 0 010 1111 0 011 . . . ", since the compression restoring module 50 knows that the remainder coding portion of the first converted signal difference value M is "010", consecutive "1" bits following "010" enable the compression restoring module 50 to identify the quotient coding portion "1111" of the next converted signal difference value M and the remainder coding portion "011" of the next converted signal difference value M. The aforesaid sequence of the bits of the other converted signal difference values M in the window compression stream Window$_{zip}$ serves an exemplary purpose, and the present disclosure is not limited thereto.

The contents of the first window compression stream Window$_{zip}$ differ from the contents of the other window compression streams Window$_{zip}$; hence, in an embodiment, the compression restoring module 50 analyzes the first 11 bits in the first window compression stream Window$_{zip}$ to obtain the actual value of the first initial datum of the ECG signal S$_{ECG}$, and then the compression restoring module 50 analyzes the subsequent bits of the first window compression stream Window$_{zip}$ (see steps S321 to S324). Therefore, the compression restoring module 50 performs decoding of the adaptive linear lossless compression encoding 32 on each window compression stream Window$_{zip}$ to restore all the converted signal difference values M.

Figure 3C:
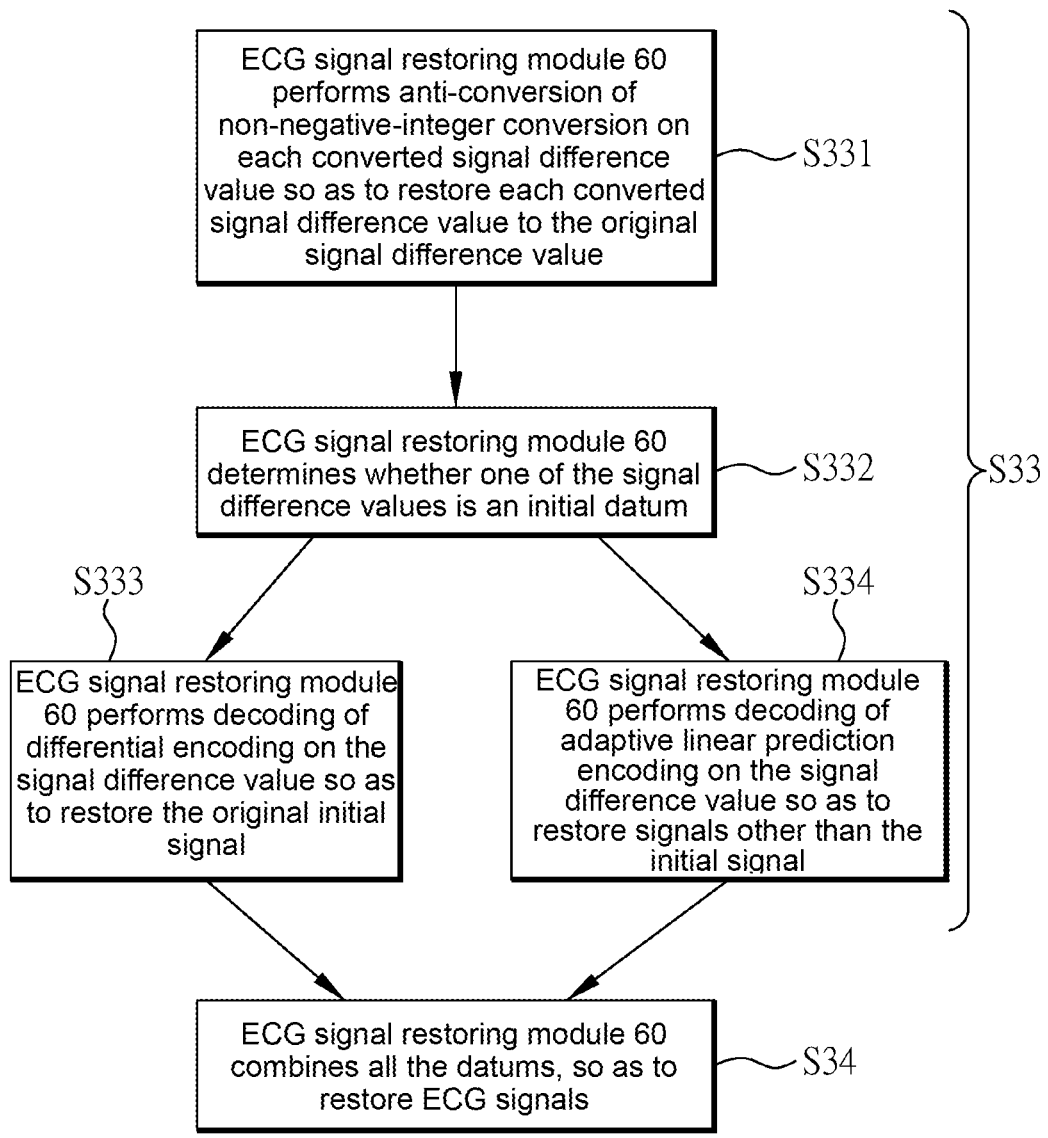
FIG. 3(C) is a flowchart of step S33 according to an embodiment of the present disclosure.

Step S33 is hereunder illustrated by an embodiment. FIG. 3(C) is a flowchart of step S33 according to an embodiment of the present disclosure. Please also refer to FIGS. 3(A) to 3(C).

First, step S331 is carried out, wherein the ECG signal restoring module 60 performs anti-conversion of the non-negative-integer conversion on each converted signal difference value M to restore each converted signal difference value M to an original signal difference value e.

Afterward, step S332 is carried out, wherein the ECG signal restoring module 60 determines whether one of the signal difference values e is an initial datum. If the determination is affirmative, step S333 is carried out, wherein the ECG signal restoring module 60 performs decoding of differential encoding on the signal difference value e so as to restore the original initial signal. If the determination is negative, step S334 is carried out, wherein the ECG signal restoring module 60 performs decoding of the adaptive linear prediction encoding on the signal difference value e so as to restore original signals other than the initial signal.

In an embodiment, since an original datum of the first initial datum is present in the first window compression stream Window$_{zip}$, the ECG signal restoring module 60 treats the first initial datum as a reference value and thus restores the other datums. In addition, the ECG signal restoring module 60 at the very least determines whether the signal difference value e corresponds to an initial datum according to the position of the signal difference value e in a sequence in the window.

In step S35, upon restoration of all the datums of the ECG signal S$_{ECG}$, the ECG signal restoring module 60 combines the datums, so as to obtain the original, complete ECG signal S$_{ECG}$.

Therefore, the ECG signal lossless compression system 1 and the ECG signal lossless compression method of the present disclosure greatly reduce the storage space and network traffic flow otherwise required for the ECG signal being transmitted and enhance the efficiency of transmission. In addition, the present disclosure is advantageous in that the encoding mechanism and the compression mechanism are timely adjusted in accordance with the characteristics of the ECG signal to reduce errors otherwise made in the compression process. Hence, when applied to existing health management systems, the present disclosure enhances system reliability greatly.

The above embodiments serve an illustrative purpose solely; hence, the scope the claims of the present disclosure shall be defined by the appended claims rather than restricted to the above embodiments.

What is claimed is:

1. An electrocardiogram (ECG) signal lossless compression system, comprising:
  a signal difference value generating module for adjusting, according to a plurality of datums preceding one of datums of an ECG signal, an adaptive linear prediction encoding corresponding to the one of datums and encoding the one of datums, so as to generate a signal difference value corresponding to each datum of the ECG signal;
  a compression module for dividing the signal difference values into a plurality of adaptive linear windows, with each said adaptive linear window comprising a specific number of the signal difference values, and performing an adaptive linear lossless compression encoding on the adaptive linear windows to achieve encoding, so as to generate a plurality of window compression streams, wherein each said adaptive linear window corresponds to a bit reference index configured to be a compression encoding parameter of the adaptive linear lossless compression encoding; and
  a compression restoring module for restoring the signal difference values compressed in the window compression stream, according to the bit reference index corresponding to each said window compression stream, and
  an ECG signal restoring module for restoring the signal difference values to the datums of the ECG signal, according to a decoding technique of the adaptive linear prediction encoding,
  wherein the adaptive linear lossless compression encoding is content-adaptive Golomb rice coding:
  wherein, before the signal difference values are divided into the adaptive linear windows, the compression module performs a non-negative-integer conversion on the signal difference values;
  wherein the non-negative-integer conversion is expressed by an equation below, $$M = \begin{cases} 2*|e| - 1, & e < 0 \\ 2*e, & e \geq 0 \end{cases}$$

wherein M denotes one of signal difference values resulting from the non-negative-integer conversion, and e denotes the one of signal difference values.

2. The ECG signal lossless compression system of claim 1, wherein the signal difference value generating module adjusts the adaptive linear prediction encoding according to numeric values, slope or directivity between the preceding datums.

3. The ECG signal lossless compression system of claim 2, wherein the signal difference value corresponding to the one of datums is defined as a difference value between the one of datums and at least one preceding datum, and the at least one preceding datum is adjusted beforehand according to the adaptive linear prediction encoding.

4. The ECG signal lossless compression system of claim 1, wherein the bit reference index of each adaptive linear window depends on magnitude of the signal difference values of the adaptive linear window.

5. The ECG signal lossless compression system of claim 4, wherein the bit reference index of an adaptive linear window is expressed by an equation below, $$k = \log 2\left(\frac{\sum_{m=0}^{m=W} |M_m|}{W}\right);$$

wherein k denotes the bit reference index of the adaptive linear window, W denotes quantity of the signal difference values of the adaptive linear window, M denotes the signal difference values resulting from the non-negative-integer conversion, n denotes sequence of the signal difference values, with n being a positive integer, and m denotes sequence of the signal difference values in the adaptive linear window, with m being a positive integer.

6. The ECG signal lossless compression system of claim 5, wherein a first window compression stream in the window compression streams comprises an original initial datum not compressed, a bit reference index and (W−1) signal difference values compressed, and the other window compression streams each comprise a bit reference index and W signal difference values compressed.

7. An (ECG) signal lossless compression method, performed with an ECG signal lossless compression system, the method comprising the steps of:
adjusting, by a signal difference value generating module, an adaptive linear prediction encoding corresponding to one of datums of an ECG signal according to a plurality of datums preceding the one of datums and encoding, by the signal difference value generating module, the one of datums, so as to generate a signal difference value corresponding to each datum of the ECG signal;
dividing, by a compression module, the signal difference values into a plurality of adaptive linear windows, with each said adaptive linear window including a specific number of said signal difference values, and performing, by the compression module, an adaptive linear lossless compression encoding on the adaptive linear windows, so as to generate a plurality of window compression streams, wherein each said adaptive linear window corresponds to a bit reference index configured to be a compression encoding parameter of the adaptive linear lossless compression encoding; and restoring, by a compression restoring module, the signal difference values compressed in the window compression streams, according to the bit reference index corresponding to each said window compression stream; and
restoring, by an ECG signal restoring module, the signal difference values to the datums of the ECG signal, using a decoding technique of the adaptive linear prediction encoding;
wherein the adaptive linear lossless compression encoding is a content-adaptive linear prediction encoding;
wherein the ECG signal lossless compression method further comprises the step of performing a non-negative-integer conversion on the signal difference values by the compression module before division of the signal difference values into the adaptive linear windows;
wherein the non-negative-integer conversion is expressed by an equation below, $$M = \begin{cases} 2*|e| - 1, & e < 0 \\ 2*e, & e \geq 0 \end{cases}$$

wherein M denotes one of signal difference values resulting from the non-negative-integer conversion, and e denotes the one of signal difference values.

8. The ECG signal lossless compression method of claim 7, further comprising the step of adjusting, by the signal difference value generating module, the adaptive linear prediction encoding according to numeric values, slope or directivity between the preceding datums.

9. The ECG signal lossless compression method of claim 8, wherein the signal difference value corresponding to the one of datums is defined as a difference value between the one of datums and at least one preceding datum, and the at least one preceding datum is adjusted beforehand by the adaptive linear prediction encoding.

10. The ECG signal lossless compression method of claim 7, wherein the bit reference index of each said adaptive linear window depends on magnitude of the signal difference values of the adaptive linear windows.

11. The ECG signal lossless compression method of claim 10, wherein the bit reference index of an adaptive linear window is expressed by an equation below, $$k = \log\left(\frac{\sum_{m=0}^{m=W} |M[n]_m|}{W}\right)$$

wherein k denotes the bit reference index of the adaptive linear window, W denotes quantity of the signal difference values of the adaptive linear window, M[n] denotes the signal difference values resulting from the non-negative-integer conversion, n denotes sequence of the signal difference values, with n being a positive integer, and m denotes sequence of the signal difference values in the adaptive linear window, with m being a positive integer.

12. The ECG signal lossless compression method of claim 11, wherein a first window compression stream of the window compression streams comprises an original initial datum not compressed, a bit reference index and (W—1) signal difference values compressed, whereas the other window compression streams each comprise a bit reference index and W signal difference values compressed.

* * * * *